United States Patent [19]
Mortazavi et al.

[11] Patent Number: 5,509,926
[45] Date of Patent: Apr. 23, 1996

[54] IMPLANTABLE MEDICAL DEVICE HAVING MEANS FOR SUPPRESSING THERMALLY INDUCED SIGNALS FROM PIEZOELECTRIC SENSORS AND METHOD THEREOF

[75] Inventors: Said Mortazavi, Sherman Oaks; Gene A. Bornzin, Camarillo, both of Calif.

[73] Assignee: Pacesetter, Inc., Sylmar, Calif.

[21] Appl. No.: 384,167

[22] Filed: Feb. 6, 1995

[51] Int. Cl.$^6$ .................................................. A61N 1/365
[52] U.S. Cl. ............................................................ 607/19
[58] Field of Search .................................. 607/17, 19, 20

[56] References Cited

U.S. PATENT DOCUMENTS

| | | | |
|---|---|---|---|
| 4,140,132 | 2/1979 | Dahl | 128/419 PG |
| 4,428,378 | 1/1984 | Anderson et al. | 128/419 PG |
| 5,014,700 | 5/1991 | Alt | 128/419 PG |
| 5,031,615 | 7/1991 | Alt | 128/419 PG |
| 5,044,366 | 9/1991 | Alt | 128/419 PG |

OTHER PUBLICATIONS

Atochem Inc., "Characteristics of KYNAR Piezo Film," Atochem Inc. Product Brochure, undated.
D. Bacharach, T. Hilden, J. Millerhagen, B. Westrum & J. Kelly, "Activity–Based Pacing: Comparison of a Device Using an Accelerometer Versus a Piezoelectric Crystal," Pace, vol. 15, Feb. 1992, pp. 188–196.
Piezo Electric Products, Inc., "Piezoceramic Design Notes," Sensors, Mar. 1984.
H. Sandler, T. Fryer and R. Westbrook, "Miniature Implantable Accelerometers.".

*Primary Examiner*—William E. Kamm
*Attorney, Agent, or Firm*—Lisa P. Weinberg; Harold C. Schloss

[57] ABSTRACT

A pyroelectric suppressor circuit for preventing undesirable thermally induced signals generated by a piezoelectric physical activity sensor from reaching processor circuitry within an implantable medical device is provided. The thermally induced signals typically have frequencies below a frequency in the range from about 0.1 mHz to about 10 mHz. The suppressor circuit provides a high-pass filter that rejects signals that have frequencies associated with thermally induced signals. Signals having frequencies greater than a frequency in the range from about 0.1 mHz to about 10 mHz, which correspond to patient activity, are passed on to processing circuitry of the implantable medical device.

23 Claims, 2 Drawing Sheets

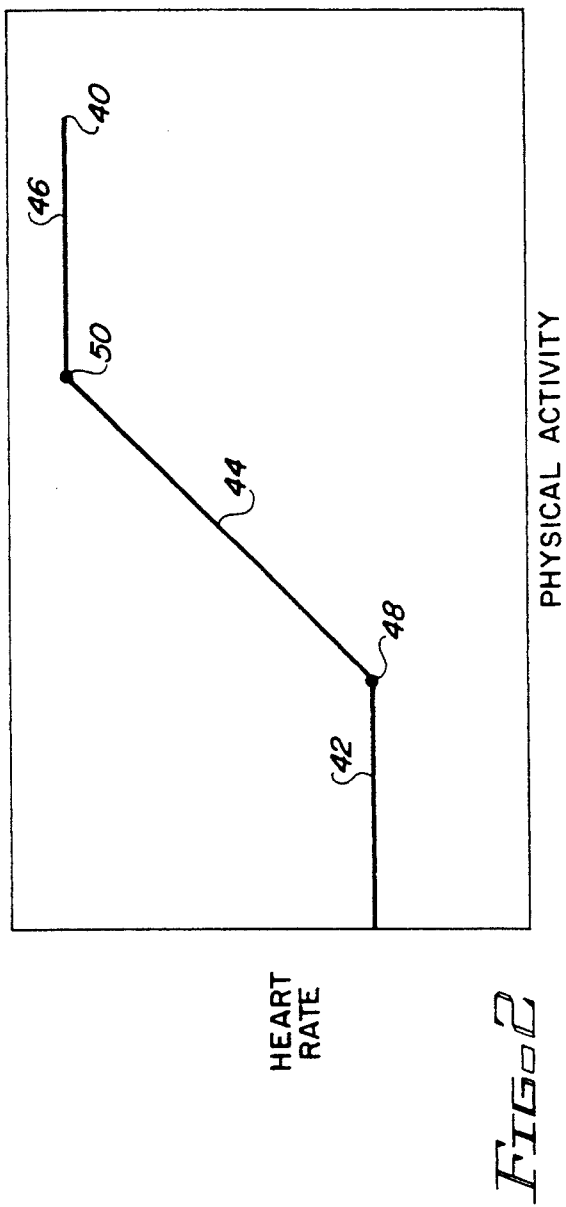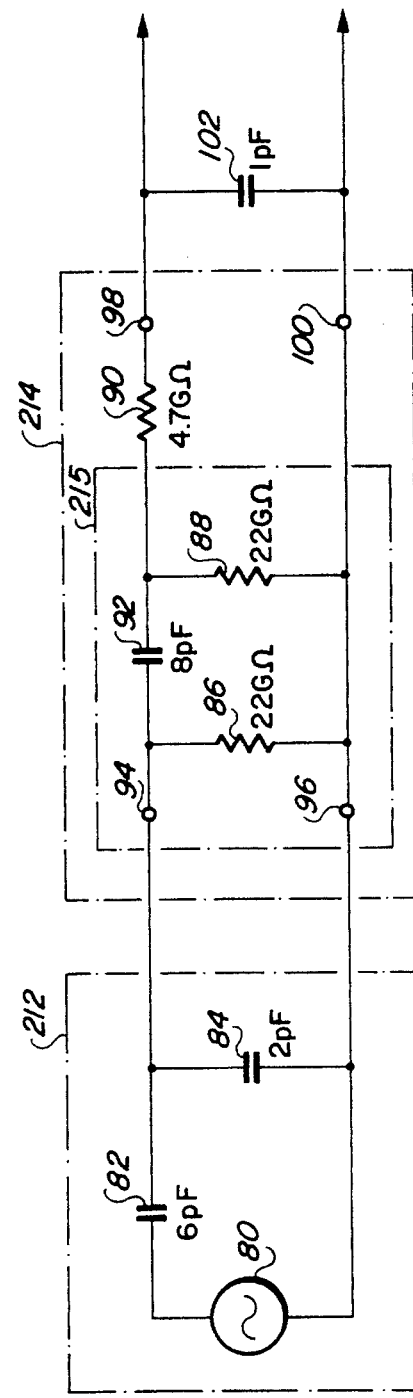
FIG. 2
FIG. 4

IMPLANTABLE MEDICAL DEVICE HAVING MEANS FOR SUPPRESSING THERMALLY INDUCED SIGNALS FROM PIEZOELECTRIC SENSORS AND METHOD THEREOF

BACKGROUND OF THE INVENTION

The present invention relates to implantable medical devices such as cardiac monitoring devices and rate-responsive pacemakers. More particularly, this invention is directed toward a pyroelectric suppressor circuit that prevents undesirable thermally induced signals generated by piezoelectric activity sensors from reaching processing circuitry within such devices.

A pacemaker is an implantable medical device which delivers electrical stimulation pulses to cardiac tissue to relieve symptoms associated with bradycardia—a condition in which a patient cannot normally maintain a physiologically acceptable heart rate. Early pacemakers delivered stimulation pulses at regular intervals in order to maintain a predetermined heart rate—typically a rate deemed to be appropriate for the patient at rest. The predetermined rate was usually set at the time the pacemaker was implanted, although in more advanced pacemakers, the rate could be set remotely after implantation.

Early advances in pacemaker technology included the ability to sense the patient's natural cardiac rhythm (i.e., the patient's intracardiac electrogram, or "IEGM"). This led to the development of "demand pacemakers"—so named because they deliver stimulation pulses only as needed by the heart. Demand pacemakers are capable of detecting a spontaneous, hemodynamically effective cardiac contraction which occurs within a predetermined time period (commonly referred to as the "escape interval") following a preceding contraction. When a naturally occurring contraction is detected within the escape interval, the demand pacemaker does not deliver a pacing pulse. The ability of demand pacemakers to avoid delivery of unnecessary stimulation pulses is desirable because by doing so, battery life is extended.

Demand pacemakers allow physicians to telemetrically adjust the length of the escape interval, which has the effect of altering the heart rate maintained by the device. However, in early devices, this flexibility only allowed for adjustments to a fixed programmed rate, and did not accommodate patients who required increased or decreased heart rates to meet changing physiological requirements during periods of elevated or reduced physical activity. Therefore, unlike a person with a properly functioning heart, a patient receiving therapy from an early demand pacemaker was paced at a constant heart rate—regardless of the level to which the patient was engaged in physical activity. Thus, during periods of elevated physical activity, the patient was subject to adverse physiological consequences, including lightheadedness and episodes of fainting, because the heart rate was forced by the pacemaker to remain constant.

The adverse effects of constant rate pacing lead to the development of "rate-responsive pacemakers" which can automatically adjust the patient's heart rate in accordance with metabolic demands. An implanted rate-responsive pacemaker typically operates to maintain a predetermined minimum heart rate when the patient is engaged in physical activity at or below a threshold level, and gradually increases the maintained heart rate in accordance with increases in physical activity until a maximum rate is reached. Rate-responsive pacemakers typically include processing and control circuitry that correlates measured physical activity to a desirable heart rate. In many rate-responsive pacemakers, the minimum heart rate, maximum heart rate, and the transition rates between the minimum heart rate and the maximum heart rate are parameters that may be adjusted to meet the needs of a particular patient.

One approach that has been considered for enabling rate-responsive pacemakers to determine an appropriate heart rate involves measuring a physiological parameter that reflects the level to which the patient is engaged in physical activity. Physiological parameters that have been considered include central venous blood temperature, blood pH level, QT time interval and respiration rate. However, certain drawbacks (such as slow response time, unpredictable emotionally-induced variations, and wide variability across individuals) render the use of these physiological parameters difficult, and accordingly, they have not been widely used in practice.

Rather, most rate-responsive pacemakers employ sensors that transduce mechanical forces associated with physical activity. These activity sensors generally contain a piezoelectric transducing element which generates a measurable electrical potential when a mechanical stress resulting from physical activity is experienced by the sensor. By analyzing the signal from a piezoelectric activity sensor, a rate-responsive pacemaker can determine how frequently pacing pulses should be applied to the patient's heart. Piezoelectric activity sensors can also be used in implantable medical devices that serve solely as cardiac monitoring devices.

Piezoelectric elements for activity sensors are commonly formed from piezoelectric ceramics, such as barium titanate. Recently, however, activity sensors have been designed which use thin films of a piezoelectric polymer, such as polyvinylidene fluoride (commonly known by the trademark KYNAR, owned by ATOCHEM North America) as the transducing element, rather than the more commonly used piezoelectric ceramics. Activity sensors so designed are described in commonly-assigned U.S. Pat. Nos. 5,383,473, entitled "Rate-Response Implantable Stimulation Device Having a Miniature Hybrid-Mountable Accelerometer Based Sensor and Method of Fabrication," and 5,425,750, entitled "Accelerometer-Based Multi-Axis Physical Activity Sensor for a Rate-Responsive Pacemaker and Method of Fabrication," now U.S. Pat. No. 5,425,750, which are hereby incorporated by reference in their entireties.

The activity sensors described in the above-incorporated patent applications, which use a resilient piezoelectric polymer as the transducing element, offer significant advantages over sensors which use piezoelectric ceramics. These advantages are largely attributable to the resiliency of the thin polymer films. For example, the piezoelectric polymer films are better able to withstand stresses that may occur during sensor fabrication, thereby reducing the cost and complexity of the fabrication process. In addition, activity sensors which use the polymer films may be designed to respond more aggressively to mechanical stresses resulting from physical activity, so that they provide stronger output signals. Indeed, the output potentials provided by activity sensors that use polyvinylidene fluoride transducing elements typically have magnitudes of about 200 mV (RMS), whereas piezoelectric crystal sensors provide output potentials which typically have magnitudes of just a few mV (RMS).

Despite the advantages associated with the use of piezoelectric polymer films in activity sensors, an unexpected difficulty has been encountered. It is known that piezoelectric materials exhibit a pyroelectric effect. More precisely, temperature fluctuations can induce mechanical stresses in piezoelectric materials, thereby causing the material to generate output potentials in response to the temperature changes. Because they are typically implanted superficially beneath the skin, implantable medical devices may often experience temperature fluctuations on the order of about 0.1° C./minute, and an overall temperature range of about 4° C. is not unusual. However, piezoelectric ceramics tend not to respond too significantly to temperature fluctuations commonly experienced by implantable medical devices. Therefore, the performance of an implantable medical device that uses a piezoelectric ceramic activity sensor would not ordinarily be adversely affected by thermally induced stresses.

However, it has been found that activity sensors which use piezoelectric polymer films exhibit a more pronounced pyroelectric effect—to an extent that may have an impact on the performance of the implantable medical devices which use such sensors. Thermally induced stresses in piezoelectric polymer sensors may cause such sensors to generate signals as large as 10 mV, which can represent a significant fraction of the total output. Thus, in the rate-responsive pacing context, a patient may experience a noticeable increase in heart rate during a bath or shower, for example, despite there being no change in activity level.

What is needed therefore is an implantable medical device which is capable of suppressing thermally induced signals generated by a piezoelectric activity sensor, so that such signals are not improperly interpreted as being indicative of physical activity. Preferably, the amount of additional circuitry required to suppress thermally induced signals should be kept to a minimum, so that the size and cost of the implantable medical device do not become prohibitive.

SUMMARY OF THE INVENTION

The above-described disadvantages and limitations associated with the use of certain known piezoelectric physical activity sensors are overcome by the present invention. With this invention, a pyroelectric suppressor circuit for use with a piezoelectric physical activity sensor of an implantable medical device is provided. The pyroelectric suppressor circuit of the present invention suppresses substantially all thermally induced sensor signals generated by such activity sensors, thereby minimizing any impact such undesirable signals may have on the performance of the implantable medical device.

The pyroelectric suppressor circuit of the present invention is particularly advantageous in the rate-responsive pacing context. The rate-responsive pacemaker includes a piezoelectric physical activity sensor—preferably one that uses a piezoelectric polymer film as the transducing element, as described in the above-incorporated U.S. Pat. Nos. 5,383,473 and 5,425,750. The signals generated by the piezoelectric activity sensor are conducted to processing circuitry within the device, which uses the signals to determine the level to which the patient is engaged in physical activity. The processing circuitry uses the measured level of physical activity to select an appropriate heart rate for the patient. The processing circuitry causes pulse generating circuitry in the rate-responsive pacemaker to maintain the patient's heart rate at the selected rate in a conventional manner (typically by adjusting the escape interval). Pacing pulses are delivered to the patient's heart through pacing leads, which may also be conventional.

For the most part, the signals generated by the piezoelectric activity sensor are representative of the level to which the patient is engaged in physical activity at any particular point in time. However, as described above, a significant fraction of the output provided by the sensor may be the result of mechanical stresses induced by temperature fluctuations of the piezoelectric material. These undesirable signals may cause the processor circuitry to make an inappropriate heart rate selection.

It has been found that thermally induced sensor signals typically have frequencies in the range from about 0.1 mHz to about 10 mHz, whereas the sensor signals that correspond to patient activity have higher frequencies (higher than about 100 mHz). The pyroelectric suppressor circuit of the present invention is therefore designed to select higher frequency signals (i.e., those signals found to be associated with physical activity), and to reject those signals having frequencies associated with thermally induced signals. To accomplish this, the pyroelectric suppressor circuit includes high-pass filter circuitry that prevents signals having frequencies less than about 10 mHz from reaching the processing circuitry within the implantable medical device.

Preferably, the high-pass filter circuitry of the pyroelectric suppressor circuit includes an 8 pF capacitor and a 22 GΩ resistor, which in combination create a zero at the origin of the transfer function of the suppressor circuit, so that at low frequencies (i.e., those frequencies associated with undesirable thermally induced signals), the transfer function approaches zero. If desired, the components of the illustrative embodiment of the present invention can be altered, so that thermally induced sensor signals having frequencies greater than 10 mHz can also be suppressed.

Although the advantages of the pyroelectric suppressor circuit of the present invention are described in connection with a rate-responsive pacemaker, the principles described herein may also be useful in other contexts. For example, certain implantable medical monitoring devices which do not provide stimulation therapy may nevertheless include a piezoelectric activity sensor to monitor the patient's physical activity level. It should also be understood that the pyroelectric suppressor circuit can be used with a piezoelectric activity sensor that does not use a piezoelectric polymer as the transducing element (such as a sensor that uses a more traditional piezoelectric material), if the sensor is found to exhibit a pronounced pyroelectric effect.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIG. 2 depicts a representative transfer curve used by the rate-responsive pacemaker of FIG. 1 to correlate measured physical activity to an appropriate heart rate;

FIG. 4 depicts an equivalent circuit representing the piezoelectric physical activity sensor of FIG. 1 and a pyroelectric suppressor circuit that may be included in the sensor circuit of FIG. 1 in accordance with the principles of the present invention.

DETAILED DESCRIPTION OF THE PREFERRED EMBODIMENT

Figure 1:
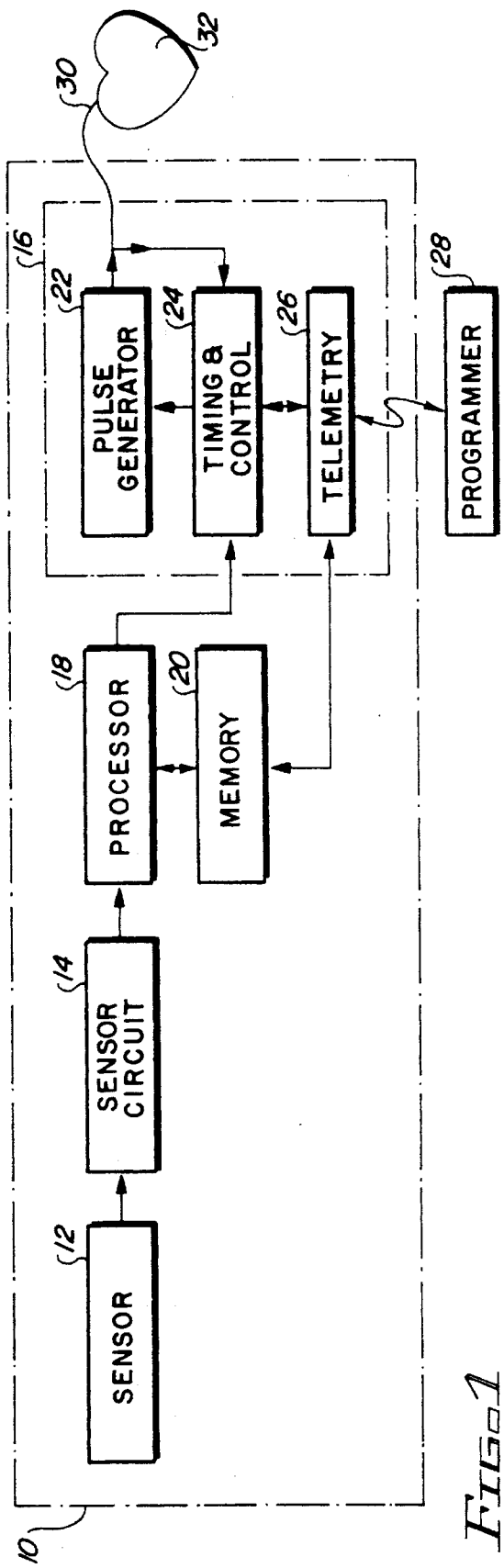
FIG. 1 is a block diagram of a rate-responsive pacemaker that includes a piezoelectric physical activity sensor, and a sensor circuit which may be adapted to include a pyroelectric suppressor circuit in accordance with the principles of the present invention.

The principles of the present invention are more easily understood when described in connection with an implantable medical device, such a rate-responsive pacemaker 10 as shown in FIG. 1. It should be understood, however, that the pyroelectric suppressor circuit described below may be used with other implantable devices, including implantable medical monitoring devices which include piezoelectric physical activity sensors.

In many respects, the pacemaker 10 operates in a conventional manner to provide pacing pulses at a rate that comfortably meets the patient's metabolic demands. More precisely, the pacemaker 10 uses signals generated by a piezoelectric physical activity sensor 12 to determine the extent to which the patient is engaged in physical activity— the measured level of activity being indicative of metabolic need. Preferably, the sensor 12 uses a piezoelectric polymer such as polyvinylidene fluoride (not shown) as a transducing element, as described in the above-incorporated U.S. Pat. Nos. 5,383,473 and 5,425,750. However, more traditional piezoelectric materials (not shown) such as barium titanate may also be used.

The signals generated by the sensor 12 are initially received by a sensor circuit 14. Several designs for the sensor circuit 14 have been used in previously known implantable medical devices, and one such design is described in greater detail below in connection with FIG. 3. However, in a preferred embodiment, a substantial modification is made to the sensor circuit 14 to implement the pyroelectric suppressor circuit of the present invention, as described in detail below in connection with FIG. 4.

In addition to the sensor 12 and the sensor circuit 14, the pacemaker 10 includes a pacemaker circuit 16 (which may be conventional), a processor 18 coupled to the sensor 12, and a memory circuit 20 coupled to the processor 18. The pacemaker circuit 16 includes a pulse generator circuit 22, a timing and control circuit 24 coupled to the pulse generator circuit 22 and to the processor 18, and a telemetry circuit 26. The telemetry circuit 26, which telemetrically communicates with an external programmer 28, is coupled within the pacemaker 10 to the memory circuit 20 and the timing and control circuit 24.

Coupled to the pulse generator circuit 22 is at least one conventional pacing lead 30 (although more pacing leads can be used if needed, as would be the case for a patient receiving dual-chamber pacing therapy). The pacing lead 30 is used to deliver pacing pulses provided by the pulse generator circuit 22 to the patient's heart 32. In addition, the pacing lead 30 senses the natural rhythm of the heart 32 (e.g., the patient's IEGM), and presents a signal indicative thereof to the timing and control circuit 24. The ability to sense the natural rhythm of the heart 32 enables the pacemaker 10 to operate in a demand mode, in which delivery of a pacing pulse is inhibited by the timing and control circuit 24 when a naturally occurring cardiac contraction is sensed during the escape interval following a preceding contraction.

Although the following description assumes that the pacemaker 10 operates in a demand mode, it should be understood that a simpler implementation is possible, in which the pacemaker 10 does not inhibit delivery of pacing pulses when naturally occurring contractions are sensed. Also, demand mode may be a telemetrically programmable feature, allowing the pacemaker 10 to be switched into and out of demand mode when desired by a physician.

In operation, the sensor 12 generates electrical potentials when the piezoelectric material of the sensor 12 is mechanically stressed. Mechanical stresses are typically caused by patient activity; however, as explained below, some mechanical stresses may be the result of temperature fluctuations. The signals generated by the sensor 12 are initially processed by the sensor circuit 14 (described below), after which they are received by the processor 18.

The processor 18 may further process the sensor signals using conventional techniques (e.g., averaging, half-wave rectification, full-wave rectification) in order to derive a measurement of the patient's current level of physical activity. The processor 18 then uses the processed sensor signals to generate a rate control signal which is provided to the timing and control circuit 24. The timing and control circuit 24 uses the rate control signal to adjust the heart rate maintained by the pacemaker 10. In a preferred embodiment, the rate control signal provided by the processor 18 adjusts the escape interval used by the timing and control circuit 24, which has the effect of increasing or decreasing the maintained heart rate.

The manner by which the pacemaker 10 adjusts the maintained heart rate in accordance with the signals provided by the sensor 12 may be understood by reference to a transfer curve 40 shown in FIG. 2. The transfer curve 40 correlates physical activity (as measured by the sensor 12 of FIG. 1) along the horizontal axis with a desired heart rate along the vertical axis. The transfer curve 40 has three segments—a minimum rate segment 42, a transition segment 44, and a maximum rate segment 46, each of which may be telemetrically varied to meet the needs of a particular patient. For example, a physician may set the minimum rate segment 42 at 60 beats per minute, and may set a first activity threshold 48 at a relatively low level of physical activity that is required before the pacemaker 10 (FIG. 1) abandons the heart rate defined by the minimum rate segment 42 in favor of a heart rate determined by the transition segment 44. The physician may set the maximum rate segment 46 at, for example, 120 beats per minute, and may set a second activity threshold 50 at a relatively high level of physical activity that is required before the pacemaker 10 (FIG. 1) discontinues using the transition segment 44 in favor of the heart rate corresponding to the maximum rate segment 46. In addition, the transition segment 44 may be telemetrically adjustable, so that changes to the maintained heart rate may be more gradual or more aggressive, depending upon the needs of a particular patient.

Information defining the transfer curve 40 is stored in the memory circuit 20 (FIG. 1) of the pacemaker 10 (FIG. 1) in a conventional manner. For example, the transfer curve 40 may be stored as a collection of discrete data points in a look-up table. Alternatively, the minimum rate segment 42 and the maximum rate segment 46 may be stored discretely, and the transition segment 44 may be stored as a mathematical relationship which is used by the processor 18 (FIG. 1) to compute the heart rate to be maintained when the determined level of physical activity as measured by the sensor 12 (FIG. 1) falls between the first activity threshold 48 and the second activity threshold 50.

Figure 3:
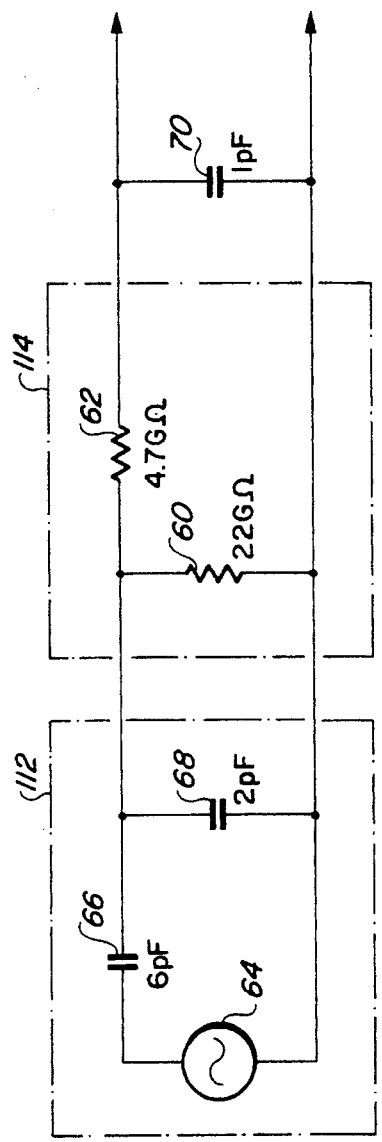
FIG. 3 depicts an equivalent circuit representing the piezoelectric physical activity sensor of FIG. 1 and a previously known circuit that has been used as the sensor circuit of FIG. 1.

As mentioned above, several designs for the sensor circuit 14 of FIG. 1 have been used in previously known rate-responsive pacemakers. One conventional sensor circuit 114 which has been used as the sensor circuit 14 of FIG. 1 is shown in FIG. 3. The previously known sensor circuit 114 is a simple resistive network that includes two resistors 60 and 62 which may have resistance values of about 22 GΩ and about 4.7 GΩ, respectively. The previously known sensor circuit 114 is coupled on one end to the sensor 12 (FIG. 1); however, in FIG. 3, the sensor 12 (FIG. 1), is depicted as an equivalent circuit 112. The equivalent circuit 112 includes a voltage source 64 and two capacitors 66 and 68 which may have capacitance values of about 6 pF and about 2 pF, respectively. The capacitor 66 represents the inherent capacitance of the piezoelectric material of the sensor 12 (FIG. 1) and the capacitor 68 represents the capacitance attributable to portions of the sensor 12 (FIG. 1) other than the piezoelectric material (e.g., connecting wires, support structure, etc.).

The opposite end of the previously known sensor circuit 114 is coupled to the processor 18 (FIG. 1), which has an input capacitance represented by a capacitor 70 having a capacitance value of about 1 pF. Once processed, the sensor signals are used to administer rate-responsive pacing therapy, as described above.

Although the previously known sensor circuit 114 provides a simple and inexpensive interface between the sensor 12 (FIG. 1) and the processor 18 (FIG. 1), there are difficulties which it does not address. The pyroelectric effect exhibited by piezoelectric materials is one such difficulty. As explained above, piezoelectric materials generate output potentials when they are mechanically stressed. When used in a physical activity sensor (such as the sensor 12 of FIG. 1), the piezoelectric material ordinarily experiences mechanical stresses when the patient engages in physical activity. However, since the pacemaker 10 (FIG. 1) cannot be maintained at a constant temperature within the patient's body (because it is implanted only superficially beneath the skin), the piezoelectric material may experience mechanical stresses resulting from temperature fluctuations.

For some piezoelectric materials, the pyroelectric effect is insignificant, and it therefore has little impact on the operation of implantable medical devices which use physical activity sensors incorporating such materials. However, certain piezoelectric materials, such as polyvinylidene fluoride, exhibit a pronounced pyroelectric effect—which may have an undesirable impact on the performance of implantable medical devices like the rate-responsive pacemaker 10 (FIG. 1). Indeed, certain types of sensors may generate signals on the order of 10 to 100 mV in response to thermally induced stresses, which can represent a significant fraction of the total output. Excessive thermally induced signals may cause a device like the pacemaker 10 (FIG. 1) to inappropriately adjust the pacing rate despite there being no change in the extent to which the patient is engaged in physical activity.

It has been found that thermally induced signals generated by piezoelectric activity sensors generally have frequencies in the range from about 0.1 mHz to about 10 mHz, whereas sensor signals that relate to patient activity have higher frequencies. The pyroelectric suppressor circuit of the present invention operates to select those signals having higher frequencies, thereby allowing those signals to be received by the processor 18 (FIG. 1), and to reject those signals having frequencies known to be indicative of thermally induced signals.

Referring now to FIG. 4, a sensor circuit 214, including a pyroelectric suppressor circuit 215, in accordance with the principles of the present invention is described. The pyroelectric suppressor circuit 214 may be included in the sensor circuit 14 (FIG. 1) to interface between the sensor 12 (FIG. 1) and the processor 18 (FIG. 1). Also shown in FIG. 4 is an equivalent circuit 212 representing the sensor 12 (FIG. 1). The equivalent circuit 212 includes a voltage source 80 and two capacitors 82 and 84 which may have capacitance values of about 6 pF and about 2 pF, respectively.

As shown in FIG. 4, the pyroelectric suppressor circuit 215 may include two resistors 86 and 88, and a capacitor 92. The sensor circuit 214 receives the sensor signals from the sensor 12 (FIG. 1) at input terminals 94 and 96, and provides output signals at output terminals 98 and 100, which are coupled to the processor 18 (FIG. 1). A capacitor 102 represents the input capacitance of the processor 18 (FIG. 1).

The preferred embodiment of the suppressor circuit 214 includes the pyroelectric suppressor circuit 215 which advantageously provides two high-pass filters for preventing sensor signals having frequencies below about 10 mHz from reaching the processor 18 (FIG. 1). As a result, the signals at the output terminals 98 and 100 more accurately reflect the true activity level of the patient.

Signals with frequencies below about 10 mHz are partially suppressed by a high-pass filter formed by the resistor 86 in combination with the capacitance of the sensor 12 (FIG. 1), which is represented by the capacitor 82. However, an additional high-pass filter is formed by the resistor 88 and the capacitor 92. The additional high-pass filter creates a zero at the origin of the transfer function of the pyroelectric suppressor circuit 215, so that at low frequencies near the origin, the transfer function approaches zero. This high-pass filter also adds a pole to the transfer function at a somewhat higher frequency. The transfer function is larger in the vicinity of this pole, which ensures that the pyroelectric suppressor circuit 215 does not block sensor signals that correspond to patient activity (signals having frequencies above about 100 mHz).

The resistor 86 preferably has a resistance value of about 22 GΩ, which is suitable when connected to the sensor 12 (FIG. 1) represented by a capacitor 82 with a capacitance value of about 6 pF. An 8 pF capacitance value for the capacitor 92 and a 22 GΩ resistance value of the resistor 88 are suitable for filtering out the undesirable low frequency signals from the sensor 12 (FIG. 1). If, however, a different activity sensor is used, the resistance value of the resistor 88 can be varied accordingly. Similarly, the illustrative 22 GΩ resistance value of the resistor 86 and the 8 pF capacitance value of the capacitor 92 can be modified. It is also possible to alter the illustrative 4.7 GΩ resistance of the resistor 90, which in combination with the 1 pF input capacitance of the processor 18 (represented by the capacitor 102), forms a low-pass filter. In addition, it may be desirable to add further high-pass filters in series with the high-pass filter formed by the resistor 88 and the capacitor 92. If a further high-pass filter is placed in the pyroelectric suppressor circuit 215, the resistance and capacitance values for the additional resistor and capacitor may preferably be selected to complement the high-pass filter arrangement of the resistor 88 and the capacitor 92.

Thus, a pyroelectric suppressor circuit is provided for preventing undesirable thermally induced signals generated by a piezoelectric physical activity sensor from reaching processing circuitry within an implantable medical device. One skilled in the art will appreciate that the present invention can be practiced by other than the described embodiments, which are presented for purposes of illustration and not of limitation, and the present invention is limited only by the claims that follow.

What is claimed is:

1. A rate-responsive pacemaker comprising:
   a piezoelectric sensor for generating sensor signals, the sensor signals including signals representative of physical activity and thermally induced signals;
   pulse generating circuitry for generating pacing pulses at an adjustable rate;
   processor circuitry for determining the rate at which the pulse generating circuitry generates pacing pulses in accordance with sensor signals generated by the piezoelectric sensor; and
   pyroelectric suppressor circuitry, coupled to the piezoelectric sensor and to the processor circuitry, for substantially limiting the sensor signals received by the processor circuitry to the signals representative of physical activity.

2. The pacemaker of claim 1, wherein the piezoelectric sensor comprises a piezoelectric polymer.

3. The pacemaker of claim 2, wherein the piezoelectric polymer comprises polyvinylidene fluoride.

4. The pacemaker of claim 1, wherein the pyroelectric suppressor circuitry comprises a first high-pass filter and a second high-pass filter connected in series.

5. The pacemaker of claim 1, wherein the pyroelectric suppressor circuitry limits substantially all of the sensor signals to those signals having frequencies greater than about 10 mHz.

6. A method of providing rate-responsive pacing therapy for use with a pacemaker, the pacemaker including a piezoelectric sensor that generates sensor signals including signals representative of physical activity and thermally induced signals, and a pulse generator that generates pacing pulses at an adjustable rate, the method comprising the steps of:
   substantially limiting the signals generated by the piezoelectric sensor to the signals representative of physical activity; and
   determining the rate at which the pulse generator generates pacing pulses in accordance with the limited sensor signals, the rate thereby being determined in accordance with the signals representative of physical activity.

7. The method of claim 6, wherein the limiting step comprises the step of filtering the sensor signals using a first and a second high-pass filters connected in series.

8. The method of claim 6, wherein the limiting step comprises the step of substantially limiting the sensor signals to those signals having frequencies greater than about 10 mHz.

9. An implantable medical device comprising:
   a processor circuit;
   a piezoelectric activity sensor that generates sensor signals including signals representative of physical activity and signals representative of temperature fluctuations; and
   a suppressor circuit, the suppressor circuit comprising:
     first and second input terminals for receiving the sensor signals from the piezoelectric activity sensor;
     first and second output terminals for providing the signals representative of physical activity to the processor circuit; and
     a high-pass filter circuit disposed between the first and second input terminals and the first and second output terminals for limiting the sensor signals to those representative of physical activity.

10. The implantable medical device of claim 9, wherein:
    the piezoelectric activity sensor includes a sensor output capacitance coupled to the first and second input terminals of the suppressor circuit;
    the second input terminal and the second output terminal are connected together and the high-pass filter circuit comprises:
      a first high-pass filter which comprises the sensor output capacitance of the piezoelectric activity sensor and a first resistor coupled across the first and second input terminals; and
      a second high-pass filter connected in series with the first high-pass filter.

11. The implantable medical device of claim 10, wherein the sensor output capacitance has a value of about 8 pF, and wherein the first resistor has a resistance value of about 22 GΩ.

12. The implantable medical device of claim 10, wherein the first resistor comprises first and second resistor terminals, and the second high-pass filter comprises:
    a second resistor having first and second resistor terminals, the second resistor terminal of the second resistor being connected to the second resistor terminal of the first resistor and to the second input terminal of the suppressor circuit, and the first resistor terminal of the second resistor being connected to the first output terminal of the suppressor circuit; and
    a capacitor having first and second capacitor terminals, the first capacitor terminal being connected to the first input terminal of the suppressor circuit, the second capacitor terminal being connected to the first terminal of the second resistor.

13. The implantable medical device of claim 12, wherein the capacitor has a value of about 8 pF, and wherein the second resistor has a resistance value of about 22 GΩ.

14. The implantable medical device of claim 9, wherein the high-pass filter circuit substantially limits the sensor signals to those having frequencies greater than about 10 mHz.

15. The implantable medical device of claim 9, wherein the suppressor circuit further comprises a low-pass filter circuit disposed between the high-pass filter circuit and the first and second output terminals.

16. The implantable medical device of claim 15, wherein the processor circuit has an input capacitance, wherein the low-pass filter circuit comprises a resistor, whereby the low-pass filter is formed by the combination of the processor circuit input capacitance and the resistor.

17. The implantable medical device of claim 16, wherein the processor circuit input capacitance has a value of about 1 pF, and wherein the resistor has a resistance value of about 47 GΩ.

18. A rate-responsive pacemaker, the rate-responsive pacemaker comprising:
    a processor circuit;
    means for providing pacing pulses to a heart, the providing means being electrically connected to the processor circuit;
    a piezoelectric activity sensor that generates sensor signals including signals representative of physical activity and signals representative of temperature fluctuations; and
    a suppressor circuit comprising:
      first and second input terminals for receiving the sensor signals from the piezoelectric activity sensor;
      first and second output terminals for providing the signals representative of physical activity to the processor circuit; and
      means disposed between the first and second input terminals and the first and second output terminals for limiting the sensor signals to those representative of physical activity.

19. The rate responsive pacemaker of claim 18, wherein:

the piezoelectric activity sensor includes a sensor output capacitance coupled to the first and second input terminals of the suppressor circuit;

the second input terminal and the second output terminal are connected together; and the means for limiting comprises:
  a first high pass filter which comprises the sensor output capacitance of the piezoelectric activity sensor and a first resistor coupled across the first and second input terminals; and
  a second high-pass filter connected in series with the first high-pass filter.

20. The rate responsive pacemaker of claim 19, wherein the sensor output capacitance has a value of about 8 pf, and wherein the first resistor has a resistance value of about 22 GΩ.

21. The rate responsive pacemaker of claim 19, wherein the second high-pass filter comprises:
  a second resistor and
  a capacitor.

22. The rate responsive pacemaker of claim 21, wherein the capacitor has a value of about 8 pF, and wherein the second resistor has a resistance value of about 22 GΩ.

23. The rate responsive pacemaker of claim 18, wherein the means for limiting substantially limits the sensor signals to those having frequencies greater than about 10 mHz.

* * * * *